United States Patent [19]

Lee

[11] Patent Number: 5,166,436
[45] Date of Patent: Nov. 24, 1992

[54] METHOD FOR THE PREPARATION OF N-ETHYLHYDROXYLAMINE HYDROCHLORIDE

[75] Inventor: George E. Lee, Somerville, N.J.

[73] Assignee: Hoechst-Roussel Pharmaceuticals Incorporated, Somerville, N.J.

[21] Appl. No.: 763,682

[22] Filed: Sep. 23, 1991

[51] Int. Cl.$^5$ ............................................ C07C 239/10
[52] U.S. Cl. .................................................... 564/301
[58] Field of Search ......................................... 564/301

[56] References Cited

U.S. PATENT DOCUMENTS 5,013,510  5/1991  Pastor et al. ...................... 564/301

OTHER PUBLICATIONS

Carpino et al., "O-Acylhydroxylamines, etc." *J. Amer. Chem. Soc.*, vol. 81 (1957) pp. 955–957.
Harris et al. "Synthesis of t-butyl Aminocarbonate, etc." *Tetrahedron Letters* vol. 24, No. 3, pp. 231–232 (1983).

*Primary Examiner*—Richard L. Raymond
*Assistant Examiner*—Peter G. O'Sullivan
*Attorney, Agent, or Firm*—Elliott Korsen

[57] ABSTRACT

A process for preparing N-ethylhydroxylamine hydrochloride which comprises reacting hydroxylamine hydrochloride with di-t-butyl dicarbonate in the presence of a base selected from sodium carbonate, potassium carbonate, sodium bicarbonate, potassium bicarbonate, sodium or potassium hydroxide or triethylamine, in a non-reactive solvent, alkylating said reaction product with an alkyl halide and then cleaving with a strong acid the tert-butyloxycarbonyl (BOC) portion of the alkylated product.

5 Claims, No Drawings

METHOD FOR THE PREPARATION OF N-ETHYLHYDROXYLAMINE HYDROCHLORIDE

BACKGROUND OF THE INVENTION

1. Field of the Invention

This invention relates to a method for the preparation of N-ethylhydroxylamine hydrochloride. More particularly, this invention relates to a novel, safe process for the preparation of N-ethylhydroxylamine hydrochloride from di-t-butyl dicarbonate (BOC anhydride) and hydroxylamine hydrochloride.

N-ethylhydroxylamine hydrochloride is useful in the preparation of pharmaceutical intermediates.

2. Background Art

The preparation of N-ethylhydroxylamine is well known, however, the preparation of this product from N,O-bis[(1,1-dimethylethoxy)-carbonyl]-hydroxylamine intermediates is novel.

Louis Carpino et al. in the Journal of the American Chemical Society, Vol. 81, 1959, pp. 955-957 discloses the synthesis of N and N,O-bis[(1,1-dimethylethoxy)-carbonyl] hydroxylamine using t-butyl azidoformate. T-butyl azidoformate is no longer used as it is a thermally unstable, shock sensitive compound which is too hazardous for any small or large scale uses, and is no longer commercially available for these reasons.

Harris et al. in Tetrahedron Letters, Vol. 24, 1983 pp. 231-32, discloses a new type of compound that can be used to acylate amines. This paper teaches the use of di-tert-butyl dicarbonate with hydroxylamine to prepare t-butyl aminocarbonate. However, the N,O-bis product was not obtained, only the O-substituted and N-substituted acylated products.

SUMMARY OF THE INVENTION

In accordance with this invention, a method is provided for preparing N-ethylhydroxylamine according to the following reaction:

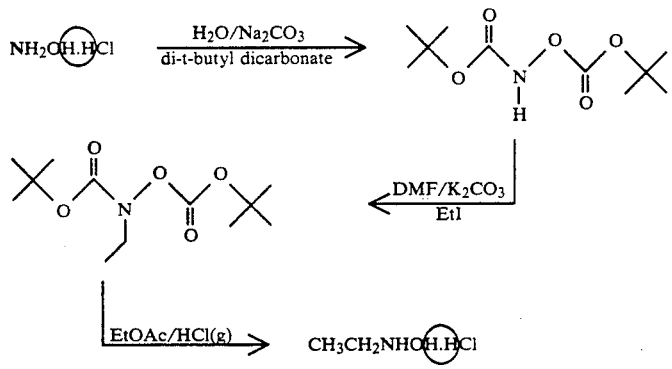

A significant advantage of the process of the invention is the preparation of N-ethylhydroxylamine in high yield and purity.

DETAILED DESCRIPTION OF THE INVENTION

Hydroxylamine hydrochloride is added to a base such as sodium carbonate, potassium bicarbonate or sodium or potassium hydroxide in a non-reactive solvent such as water, dichloromethane or dioxane, then treated with di-t-butyl dicarbonate added over a period of 30 minutes to 6 hours at 10° to 60° C. Unexpectedly, N,O-bis-BOC-hydroxylamine is isolated. This is unexpected because the literature suggests that the N,O-bis product is only available when the hydroxylamine hydrochloride is reacted with t-butyl azidoformate.

The pH of the solution is adjusted such that it is a basic solution with a pH between 7 to 11. Any of the aforementioned bases can be used and the pH depends on the choice of base.

The reaction can be run with any solvent that will not react with the base or di-tert-butyl dicarbonate. Therefore it is preferred that primary or secondary amines, alcohols or thiols not be used. Water is the preferred solvent.

The N,O-bis-BOC-hydroxylamine is isolated following extraction with toluene, concentration with azeotropic removal of t-butanol and crystallization from hexane.

The N,O-bis-BOC-hydroxylamine can be alkylated in the following manner. The product, in DMF, is treated with a base such as potassium or sodium carbonate or potassium-t-butoxide or other alkali metal alkoxides and an alkylhalide such as ethyl iodide or ethyl bromide. This alkylation reaction is typically conducted at a temperature of 0° to 70° C., for 15 minutes to 6 hours. Preferably, the reaction is conducted at a temperature range of 25° to 35° C. for 30 minutes to 1 hour. The temperature of the alkylation step is controlled by the boiling point of the alkylating agent.

N-ethyl-N,O-bis-BOC-hydroxylamine is isolated as an oil following dilution with water, extraction and concentration in vacuo.

This oil, in ethyl acetate, is treated with HCl or other suitable acids at 30° to 40° C. for 30 minutes to 3 hours to cleave the N,O-bis-BOC portion of the compound to yield N-ethylhydroxylamine hydrochloride in high yield, when anhydrous HCl is used. In order to smoothly cleave the BOC group, a large amount of hydrochloric acid is required. Greater than 2 equivalents of the HCl is required to cleave the BOC group. The amount of HCl is within a range of 2 to 7 equivalents with the preferred range being between 5 and 6 equivalents of the acid.

The ratio of the reactants in the first step is two moles of the BOC catalyst per mole of hydroxylmine hydrochloride. However, the reaction can be run at a ratio of up to 3 moles of the BOC catalyst per mole of hydrochloride without significant decrease in yield.

The inventive method may be further illustrated by the following example. All parts, proportions, ratios and percentages are by weight unless otherwise indicated.

EXAMPLE 1 a. Conversions of hydroxylamine hydrochloride to N,O-bis-BOC-hydroxylamine

Hydroxylamine hydrochloride (1 mole) is added to $Na_2CO_3$ (1.25 moles) in $H_2O$ (500 ml) then treated with di-t-butyl dicarbonate (BOC) (2.0-2.2 equiv) added over 3 hours at 35°-40° C. Following extraction with toluene (2:1 v/v), concentration with azeotropic removal of t-butanol and crystallization from hexane (1:1 v/v), N,O-bis-BOC-hydroxylamine, m.p. 70°-72° C., is isolated in high yield. The product from 3 similar reactions was combined and recrystallized from hexane to give 629 g of purified product.

b. Alkylation to N-ethyl-N,O-bis-BOC-hydroxylamine

N,O-bis-BOC-hydroxylamine (1.35 mole) in dimethylformamide (3:1 v/v) is treated with potassium carbonate (1.25 equiv, milled) and ethyl iodide (1.025 equiv). The ethyl iodide is added over ¾ hour at 30° C. Complete conversion to N-ethyl-N,O-bis-BOC-hydroxylamine was observed by thin layer chromatography at 30 minutes/30° C. following addition of the ethyl iodide. The product (704.7 g) is isolated as an oil from 2 similarly run reactions following dilution with $H_2O$ (8:1 v/v), extraction with toluene (2:1 v/v), washing with water (4×3:1 v/v) and concentration in vacuo.

c. Cleavage to N-ethylhydroxylamine hydrochloride

N-Ethyl-N,O-bis-BOC-hydroxylamine (1.35 mole), in ethyl acetate (3:1 v/v), is treated with HCl (5.5 equiv, anhy.) at 37° C. added over 1¾ hours. The product was concentrated in vacuo to give 129.8 g of N-ethylhydroxylamine hydrochloride in high yield.

I claim:

1. A process for preparing N-ethylhydroxylamine hydrochloride which comprises reacting hydroxylamine hydrochloride with di-t-butyl dicarbonate in the presence of a base selected from sodium carbonate, potassium carbonate, sodium bicarbonate, potassium bicarbonate, sodium or potassium hydroxide or triethylamine, in a non-reactive solvent, alkylating said reaction product with an alkyl halide and then cleaving with a strong acid the tert-butyloxycarbonyl (BOC) portion of the alkylated product.

2. The process as defined in claim 1 wherein the alkylating agent is ethyl iodide or ethyl bromide.

3. The process as defined in claim 2 wherein the solvent is water, dichloromethane or dioxane.

4. The process as defined in claim 2 wherein the base is sodium carbonate or potassium carbonate.

5. The process as defined in claim 4 wherein the base is sodium carbonate, the solvent is water, the alkylating agent is ethyl iodide and the acid is hydrochloric acid.

* * * * *